United States Patent
Vernier et al.

(10) Patent No.: US 8,563,566 B2
(45) Date of Patent: *Oct. 22, 2013

(54) NAPHTHYRIDINE DERIVATIVES AS POTASSIUM CHANNEL MODULATORS

(75) Inventors: Jean-Michel Vernier, Laguna Niguel, CA (US); Martha De la Rosa, San Diego, CA (US)

(73) Assignee: Valeant Pharmaceuticals International, Aliso Viejo, CA (US)

( * ) Notice: Subject to any disclaimer, the term of this patent is extended or adjusted under 35 U.S.C. 154(b) by 1083 days.

This patent is subject to a terminal disclaimer.

(21) Appl. No.: 12/181,126

(22) Filed: Jul. 28, 2008

(65) Prior Publication Data

US 2009/0170885 A1   Jul. 2, 2009

Related U.S. Application Data

(60) Provisional application No. 60/962,862, filed on Aug. 1, 2007.

(51) Int. Cl.
| | |
|---|---|
| A01N 43/54 | (2006.01) |
| A61K 31/505 | (2006.01) |
| C07D 401/00 | (2006.01) |
| C07D 403/00 | (2006.01) |
| C07D 405/00 | (2006.01) |
| C07D 409/00 | (2006.01) |
| C07D 411/00 | (2006.01) |
| C07D 413/00 | (2006.01) |
| C07D 417/00 | (2006.01) |
| C07D 419/00 | (2006.01) |

(52) U.S. Cl.
USPC .......................................... 514/275; 544/324

(58) Field of Classification Search
None
See application file for complete search history.

(56) References Cited

U.S. PATENT DOCUMENTS

| | | |
|---|---|---|
| 4,181,803 A | 1/1980 | Morita et al. |
| 4,554,281 A | 11/1985 | vonBebenburg et al. |
| 4,668,684 A | 5/1987 | Tibes et al. |
| 4,778,799 A | 10/1988 | Tibes et al. |
| 4,923,858 A | 5/1990 | Engel et al. |
| 4,923,974 A | 5/1990 | Ueda et al. |
| 5,032,591 A | 7/1991 | Evans et al. |
| 5,162,346 A | 11/1992 | Lobisch et al. |
| 5,234,947 A | 8/1993 | Cherksey |
| 5,262,419 A | 11/1993 | Aberg et al. |
| 5,284,861 A | 2/1994 | Lobisch et al. |
| 5,384,330 A | 1/1995 | Dieter et al. |
| 5,428,039 A | 6/1995 | Cohen |
| 5,502,058 A | 3/1996 | Mayer et al. |
| 5,643,921 A | 7/1997 | Grover |
| 5,679,706 A | 10/1997 | D'Alonzo et al. |
| 5,760,007 A | 6/1998 | Shank |
| 5,800,385 A | 9/1998 | Demopulos et al. |
| 5,849,789 A | 12/1998 | Rostock et al. |
| 5,852,053 A | 12/1998 | Rostock et al. |
| 5,858,017 A | 1/1999 | Demopulos et al. |
| 5,860,950 A | 1/1999 | Demopulos et al. |
| 5,914,425 A | 6/1999 | Meisel et al. |
| 5,925,634 A | 7/1999 | Olney |
| 5,965,582 A | 10/1999 | Lebaut et al. |
| 6,117,900 A | 9/2000 | Rundfeldt et al. |
| 6,211,171 B1 | 4/2001 | Sawynok et al. |
| 6,218,411 B1 | 4/2001 | Koga |
| 6,265,417 B1 | 7/2001 | Carroll |
| 6,281,211 B1 | 8/2001 | Cai et al. |
| 6,326,385 B1 | 12/2001 | Wickenden et al. |
| 6,348,486 B1 | 2/2002 | Argentieri et al. |
| 6,395,736 B1 | 5/2002 | Parks et al. |

(Continued)

FOREIGN PATENT DOCUMENTS

| | | |
|---|---|---|
| CA | 2542434 | 5/2005 |
| DE | 3337593 | 10/1983 |

(Continued)

OTHER PUBLICATIONS

Wolff et. al., "Burger's Medicinal Chemistry and Drug Discovery," 5th Ed. Part 1, pp. 975-977 (1995).*
Banker, et. al., (1996), Modern Pharmaceuticals, p. 596.*
Vippagunta et. al. Advanced Drug Delivery Reviews 48 (2001) 3-26.*
Armand et al., "Effects of retigabine (D-23129) on different patterns of epileptiform activity induced by 4-aminopyridine in rat entorhinal cortex hippocampal slices," *Naunyn-Schmiedeberg's Arch Pharmacol* 359:33-39 (1999).

(Continued)

*Primary Examiner* — Jeffrey Murray
(74) *Attorney, Agent, or Firm* — Jones Day; Len Smith (Valeant)

(57) ABSTRACT

This invention provided compounds of formula I

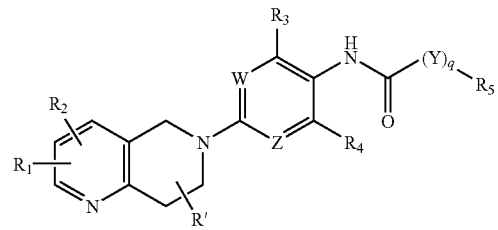

where W and Z are, independently, CH or N, and where other substituents are defined herein. Such compounds are potassium channel modulators.

The invention also provides a composition comprising a pharmaceutically acceptable carrier or excipient and at least one of the following: a pharmaceutically effective amount of a compound of formula I; a pharmaceutically acceptable salt of a compound of formula I; a pharmaceutically acceptable ester of a compound of formula I. The invention also provides a method of preventing or treating a disease or disorder which is affected by activities of potassium channels, comprising administering to a patient in need thereof a therapeutically effective amount of a compound of formula I or a salt or ester or solvate thereof.

43 Claims, No Drawings

(56) References Cited

U.S. PATENT DOCUMENTS

| | | |
|---|---|---|
| 6,451,857 B1 | 9/2002 | Hurtt et al. |
| 6,469,042 B1 | 10/2002 | Hewawasam et al. |
| 6,472,165 B1 | 10/2002 | Rundfeldt et al. |
| 6,495,550 B2 | 12/2002 | McNaughton-Smith et al. |
| 6,500,455 B1 | 12/2002 | Frantsits |
| 6,537,991 B1 | 3/2003 | Shaw et al. |
| 6,538,004 B2 | 3/2003 | Drizin |
| 6,538,151 B1 | 3/2003 | Meisel et al. |
| RE38,115 E | 5/2003 | Smith et al. |
| 6,589,986 B2 | 7/2003 | Bowlby et al. |
| 6,593,335 B1 | 7/2003 | Carroll |
| 6,642,209 B1 | 11/2003 | Fukunaga |
| 6,645,521 B2 | 11/2003 | Cassel |
| 6,737,422 B2 | 5/2004 | McNaughton-Smith et al. |
| 6,762,320 B2 | 7/2004 | Jolidon et al. |
| 6,831,087 B2 | 12/2004 | Alanine et al. |
| 7,045,551 B2 | 5/2006 | Wu et al. |
| 7,160,684 B2 | 1/2007 | Argentieri et al. |
| 7,250,511 B2 | 7/2007 | Bavetsias |
| 7,309,713 B2 | 12/2007 | Rundfeldt et al. |
| 7,419,981 B2 | 9/2008 | Field et al. |
| 7,786,146 B2 | 8/2010 | Vernier et al. |
| 2002/0013349 A1 | 1/2002 | Wickenden |
| 2002/0015730 A1 | 2/2002 | Hoffmann et al. |
| 2002/0183395 A1 | 12/2002 | Argentieri |
| 2004/0198724 A1 | 10/2004 | McNaughton-Smith et al. |
| 2005/0089473 A1 | 4/2005 | Black et al. |
| 2005/0089559 A1 | 4/2005 | Szelenyi |
| 2005/0090547 A1 | 4/2005 | Szelenyi |
| 2005/0202394 A1 | 9/2005 | Dobson |
| 2005/0277579 A1 | 12/2005 | Krishnan et al. |
| 2006/0155121 A1 | 7/2006 | Tornoe et al. |
| 2006/0167087 A1 | 7/2006 | Greve et al. |
| 2007/0066612 A1 | 3/2007 | Khanzhin et al. |
| 2008/0139610 A1 | 6/2008 | Vernier et al. |
| 2008/0318979 A1* | 12/2008 | Vernier et al. ............. 514/258.1 |
| 2009/0170885 A1 | 7/2009 | Vernier et al. |
| 2011/0039827 A1 | 2/2011 | Blackburn et al. |
| 2011/0104315 A1 | 5/2011 | Sun et al. |

FOREIGN PATENT DOCUMENTS

| | | |
|---|---|---|
| DE | 3604575 A1 | 8/1986 |
| DE | 103 49 729.3 | 10/2003 |
| DE | 103 59 335 | 5/2005 |
| EP | 189281 A1 | 8/1986 |
| EP | 0 343 429 | 5/1989 |
| EP | 1 334 972 | 8/2003 |
| EP | 1 407 768 | 4/2004 |
| EP | 1 813 285 A1 | 8/2007 |
| JP | 2000 14350 | 5/2000 |
| JP | 2000 143510 A | 5/2000 |
| RU | 2006117525 | 12/2005 |
| WO | 98/49152 | 11/1998 |
| WO | WO 00/55137 | 9/2000 |
| WO | WO 00/59487 A2 | 10/2000 |
| WO | WO 00/59508 | 10/2000 |
| WO | WO 01/01970 | 1/2001 |
| WO | WO 01/01972 A2 | 1/2001 |
| WO | WO 01/09612 | 2/2001 |
| WO | WO 01/22953 A2 | 4/2001 |
| WO | WO 02/080898 | 10/2002 |
| WO | WO 03/020706 | 3/2003 |
| WO | WO 03/097586 | 11/2003 |
| WO | WO 03/106454 A1 | 12/2003 |
| WO | WO 2004/058739 | 7/2004 |
| WO | WO 2004/080950 | 9/2004 |
| WO | WO 2004/082677 | 9/2004 |
| WO | WO 2004/096767 | 11/2004 |
| WO | WO 2004/105795 | 12/2004 |
| WO | WO 2005/039576 A1 | 5/2005 |
| WO | WO 2005/048975 | 6/2005 |
| WO | WO 2005/087754 | 9/2005 |
| WO | WO 2005/100349 | 10/2005 |
| WO | WO 2006/029623 | 3/2006 |
| WO | WO 2006/092143 | 9/2006 |
| WO | 2008/020607 | 2/2008 |
| WO | WO 2008/024398 | 2/2008 |
| WO | WO 2008/066900 | 6/2008 |

OTHER PUBLICATIONS

Armijo et al., "Ion channels and epilepsy," *Curr Pharm Des.* 11:1975-2003 (2005).

Barhanin, M., et al., "$K_vLQT1$ and ISK (minK) proteins associate to form the $I_{Ks}$ cardiac potassium current," *Nature* 384(6604):78-80 (1996).

Beeby et al. "The synthesis and properties of 2:7-Disubstituted 1:2:3:4-tetrahydroisoquinolines," *J. Chem. Soc.* ¶ 385, 1799-1803 (1949).

Bialer et al., "Progress report on new antiepileptic drugs: a summary of the fourth Eilat conference (EILAT IV)," *Epilepsy Res.* 34:1-41 (1999).

Bialer, "Progress report on new antiepileptic drugs: a summary of the Sixth Eilat Conference (EILAT VI)," *Epilepsy Res.* 51:31-71 (2002).

Bialer, "Progress report on new antiepileptic drugs: a summary of the Seventh Eilat Conference (EILAT VII)," *Epilepsy Res.* 61:1-48 (2004).

Biervert et al., "A potassium channel mutation in neonatal human epilepsy," *Science* 279:403-406 (1998).

Blackburn-Munro and Jensen, "The anticonvulsant retigabine attenuates nociceptive behaviours in rat models of persistent and neuropathic pain," *Eur J Pharmacol.* 460: 109-116 (2003).

Brown and Adams, "Muscarinic suppression of a novel voltage-sensitive $K^+$ current in a vertebrate neurone," *Nature* 283:673-676 (1980).

Brown, D.A., *Ion Channels*, T. Narahashi, Ed. (Plenum Press, New York) pp. 55-94 (1988).

Charlier et al., "A pore mutation in a novel KQT-like potassium channel gene in an idiopathic epilepsy family," *Nat Genet.* 18:53-55 (1998).

Cooper et al., "Colocalization and coassembly of two human brain M-type potassium in channel subunits that are mutated in epilepsy." *Proc Natl Acad Sci USA* 97:4914-4919 (2000).

Delmas and Brown, "Pathways modulating neural KCNQ/M (Kv7) potassium channels," *Nat Rev Neurosci.* 6:850-862 (2005).

Dickenson al., "Neurobiology of neuropathic pain: mode of action of anticonvulsants," *Eur. J. Pain* 6:51-60 (2002).

Dost et al., "The anticonvulsant retigabine potently suppresses epileptiform discharges in the low Ca ++ and low Mg++ model in the hippocampal slice preparation," *Epilepsy Res.* 38:53-56 (2000).

Friedel and Fitton, "Flupirtine: a review of its analgesic properties, and therapeutic efficacy in pain states," *Drugs* 45:548-569 (1993).

Hiller et al., "Retigabine N-glucuronidation and its potential role in enterohepatic circulation," *Drug Metab Dispos.* 27(5):605-612 (1999).

Hunt and Mantyh, "The molecular dynamics of pain control," *Nat Rev Neurosci.* 2:83-91 (2001).

Jentsch, "Neuronal KCNQ potassium channels; physiology and role in disease," *Nat. Rev Neurosci.*, 1:21-30 (2000).

Jiang et al., "X-ray structure of a voltage-dependent K+ channel," *Nature* 423:33-41 (2003).

Kharkovets et al., "Mice with altered KCNQ4 $K^+$ channels implicate sensory outer hair cells in human progressive deafness," *EMBO J* 25:642-652 (2006).

Kibbe *Handbook of Pharmaceutical Excipients* (Pharmaceutical Press, London) (2000).

Kubisch et al., "KCNQ4, a novel potassium channel expressed in sensory outer hair cells, is mutated in dominant deafness," *Cell* 96:437-446 (1999).

Lamas et al., "Effects of a cognition-enhancer, linopirdine (DuP 996), on M-type potassium currents ($I_{K(M)}$) and some other voltage- and ligand-gated membrane currents in rat sympathetic neurons," *Eur. J Neurosci.*, 9:605-616 (1997).

Lee et al., "Structure of the KvAP voltage-dependent $K^+$ channel and its dependence on the lipid membrane," *Proc Natl Acad Sci USA* 102:15441-15446 (2005).

(56) References Cited

OTHER PUBLICATIONS

Long et al., "Crystal Structure of a mammalian voltage-dependent *Shaker* family K+ channel," *Science* 309:897-903 (2005).
Main et al., "Modulation of KCNQ2/3 potassium channels by the novel anticonvulsant retigabine," *Mol. Pharmacol.* 58:253-262 (2000).
Marrion, "Control of M-currents," *Annu Rev Physiol.* 59:483-504 (1997).
Parcej and Eckhardt-Strelau, Structural characterization of neuronal voltage-sensitive K+ channels heterologously expressed in *Pichia pastoris*, *J Mol Biol* 333:103-116 (2003).
Passmore et al., "KCNQ/M currents in sensory neurons: significance for pain therapy," *J. Neurosc.* 23:7227-7236 (2003).
Porter et al., "Retigabine," *Neurotherapeutics* 4:149-154 (2007).
Reich et al., "Design and synthesis of novel 6,7-imidazotetrahydroquinoline inhibitors of thymidylate synthase using iterative protein crystal structure analysis," J. Med. Chem. 35:847-858 (1992).
Rogawski, MA, "KCNQ2/KCNQ3 K+ channels and the molecular pathogenesis of epilepsy: implications for therapy," *Trends Neurosci.* 23:393-398 (2000).
Rostock et al., "A new anticonvulsant with broad spectrum activity in animal models of epileptic seizures," *Epilepsy Res*.23:211-223 (1996).
Rundfeldt et al., "Multiple actions of the new anticonvulsant D-23129 on voltage-gated inward currents and GABA-induced currents in cultured neuronal cells (abstract)," *Naunvn-Schmiedeberg's Arch Pharmacol* 351 (Suppl):R160 (1995).
Rundfeldt, "Characterization of the K+ channel opening effect of the anti-convulsant retigabine in PC12 cells," *Epilepsy Res*.35:99-107 (1999).
Rundfeldt, "The new anticonvulsant retigabine (D23129) acts as an opener of K+ channels in neuronal cells," Eur J Pharmacol. 336:243-249 (1997).
Schroeder et al., "KCNQ5, a novel potassium channel broadly expressed in brain, mediates M-type currents," *J. Biol. Chem.* 275:24089-24095 (2000).
Schroeder, "Moderate loss of function of cyclic-AMP-modulated KNCQ2/KCNQ3 K+ channels causes epilepsy," *Nature* 396:687-690 (1998).
Singh et al., "A novel potassium channel gene, KCNQ2, is mutated in an inherited epilepsy of newborns," *Nat Genet.* 18:25-29 (1998).
Suzuki and Dickenson, "Neuropathic pain: nerves bursting with excitement," *NeuroReport* 11:R17-R21 (2000).
Tatulian and Brown, "Effect of the KCNQ potassium channel opener retigabine on single KCNQ2/3 channels express in CHO cells," *J Physiol.* 549:57-63 (2003).
Tatulian et al., "Activation of expressed KCNQ potassium currents and native neuronal M-type potassium currents by the anti-convulsant drug retigabine," *J. Neurosci.* 21:5535-5545 (2001).
Tober et al., "D-23129: a potent anticonvulsant in the amygdala kindling model of complex partial seizures," *Eur J Pharmacol*, 303:163-169 (1996).
Von Bebenburg et al., "Substituierte Polyaminopyridine" *Chemiker-Zeitung* 103:387-399 (1979). (German language article attached.).
Wang et al., KCNQ2 and KCNQ3 potassium channel subunits: molecular correlates of the M-channel, *Science* 282:1890-1893 (1998).
Wang et al., "Positional cloning of a novel potassium channel gene: KVLQT1 mutations cause cardiac arrhythmias," *Nat Genet* 12:17-23 (1996).
Watanbe et al., "Disruption of the epilepsy KCNQ2 gene results in neural hyperexcitability," *J. Neurochem* 75:28-33 (2000).
Wickenden et al., "KCNQ potassium channels: drug targets for the treatment of epilepsy and pain," *Exp. Opin Thera Patents* 14(4): 457-469 (2004).
Wickenden et al., "Retigabine, a novel anti-convulsant, enhances activation of KCNQ2/Q3 potassium channels," *Mol. Pharmacol.* 58:591-600 (2000).
Wuttke, "The new anticonvulsent retigabine favors voltage-dependent opening of the Kv7.2 (KCNQ2) channel by binding to its activation gate," *Mol. Pharmacol.* 67:1009-1017 (2005).
West, Solid State Chemistry and its Applications (John Wiley & Sons, New York) pp. 358 and 365 (1988).
Said, "Glutamate receptors and asthmatic airway disease," Trends. Pharmacol. Sci. 20(4):132-134 (1999).
Xue et al., "Rational design, synthesis and structure-activity relationships of a cyclic succinate series of TNF-alpha converting enzyme inhibitors. Part 1: lead identification," Bioorg. Med. Chem. Lett. 13(24):4293-4297 (2003).
Lange et al., "Refinement of the binding site and mode of action of the anticonvulsant Retigabine on KCNQ K+ channels," Mol. Pharmacol. 75(2):272-280 (2009).
Beck et al., "Kreuzschmerzen in der Gynaekologischen praxis," Ginaekologe, Springer Verlag, Berlin Germany 35(5):490-494 (2002).
Kuo et al., "Inhibition of Na+ current by diphenhydramine and other diphenyl compounds: molecular determinants of selective binding to the inactivated channels," *Mol. Pharmacol.* 57(1):135-143(2000).
Patani, "Bioisosterism: A Rational Approach in Drug Design," *Chem. Rev.* 96:3147-3176 (1996).
Touboul et al. "A Comparative evaluation of the effects of Propafenone and lidocaine on early ventricular arrhythmias after acute myocardial infarction," *Eur. Heart J.* 9:118-1193 (1988). Abstract.
Vippagunta et al., "Crystalline solids," *Adv. Drug Deliv. Rev.* 48:3-26 (2001).
Wolf (ed.), Burger's Medicinal Chemistry and Drug Discovery, 5th Edition vol. 1: Principles and Practice, John Wiley & Sons, New York, pp. 975-977 (1995).
Wu et al., "Regulatory perspectives of Type II prodrug development and time-dependent toxicity management: nonclinical Pharm/Tox analysis and the role of comparative toxicology," *Toxicology* 236:1-6 (2007).
Zani et al., "Sodium channels are required during in vivo sodium chloride hyperosmolarity to stimulate increase in intestinal endothelial nitric oxide production," *Am. J. Physiol. Heart Circ. Physiol.* 288:H89-H95 (2005).

\* cited by examiner

NAPHTHYRIDINE DERIVATIVES AS POTASSIUM CHANNEL MODULATORS

CROSS-REFERENCE TO RELATED APPLICATIONS

This application claims priority under 35 U.S.C. §119(e) to U.S. Provisional application Ser. No. 60/962,862, filed Aug. 1, 2007, the entire contents of which is incorporated herein by reference.

FIELD OF THE INVENTION

This invention concerns novel compounds that modulate potassium channels. The compounds are useful for the treatment and prevention of diseases and disorders which are affected by activities of potassium ion channels. One such condition is seizure disorders.

BACKGROUND OF THE INVENTION

Retigabine (N-[2-amino-4-(4-fluorobenzylamino)phenyl] carbamic acid, ethyl ester] (U.S. Pat. No. 5,384,330) has been found to be an effective treatment of seizure disorders in children. Bialer, M. et al., Epilepsy Research 1999, 34, 1-41. Retigabine has also been found to be useful in treating pain, including neuropathic pain. Blackburn-Munro and Jensen, Eur. J. Pharmacol. 2003, 460, 109-116; Wickenden, A. D. et al., Expert Opin. Ther. Patents 2004 14-(4).

A form of epilepsy known as "benign familial neonatal convulsions" has been associated with mutations in the KCNQ2/3 channels. Biervert, C. et al., Science 1998, 27, 403-06; Singh, N. A. et al., Nat. Genet. 1998, 18, 25-29; Charlier, C. et al., Nat. Genet. 1998, 18, 53-55, Rogawski, Trends in Neurosciences 2000, 23, 393-398. Subsequent investigations have established that the primary site of retigabine action is the KCNQ2/3 channel. Wickenden, A. D. et al., Mol. Pharmacol. 2000, 58, 591-600; Main, M. J. et al., Mol. Pharmcol. 2000, 58, 253-62. Retigabine has been shown to increase the conductance of the channels at the resting membrane potential and to bind the activation gate of the KCNQ 2/3 channel. Wuttke, T. V. et al., Mol. Pharmacol. 2005, 67, 1009-1017. With increased sophistication of research in this area, retigabine has also been shown to increase neuronal M currents and to increase the channel open probability of KCNQ 2/3 channels. Delmas, P. and Brown, D. A. Nat. Revs Neurosci., vol. 6, 2005, 850-62; Tatulian, L. and Brown, D. A., J. Physiol., (2003) 549, 57-63.

The recognition of retigabine as a potassium channel modulator has prompted numerous searches for other potassium channel modulators among compounds with various structural features in common with retigabine.

BRIEF DESCRIPTION OF THE INVENTION

In one embodiment, this invention provides a compound of formula I

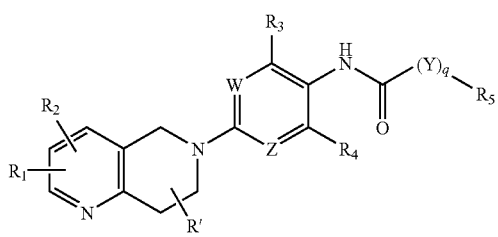

where W and Z are, independently, CH or N; Y is $CH_2$, O or NH;

where $R_1$ and $R_2$, are, independently, H, halogen, $CH_2F$, $CHF_2$, $CF_3$, $CF_2CF_3$, $C_1$-$C_6$ alkyl, C(=O)$C_1$-$C_6$ alkyl, $CH_2C$(=O)$C_1$-$C_6$ alkyl, NH—$C_1$-$C_6$ alkyl, NHC(=O)$C_1$-$C_6$ allyl, C(=O)N($CH_3$)$_2$, C(=O)N(Et)$_2$, C(=O)NH—$C_1$-$C_6$ alkyl, C(=O)O$C_1$-$C_6$ alkyl, OC(=O)$C_1$-$C_6$ allyl, O$C_1$-$C_6$ alkyl, S$C_1$-$C_6$ alkyl, $C_3$-$C_6$ Cycloalkyl, $(CH_2)_m C_3$-$C_6$ cycloalkyl, $C_3$-$C_6$ cycloalkenyl, $(CH_2)m C_3$-$C_6$ cycloalkenyl, $C_2$-$C_6$ alkenyl, $C_2$-$C_6$ alkynyl, Ari, $(CH_2)$n, Ari, phenyl, pyridyl, pyrrolyl, $(CH_2)_m$imidazolyl, $(CH_2)_m$pyrazyl, furyl, thienyl, $(CH_2)_m$ oxazolyl, $(CH_2)_m$isoxazolyl, $(CH_2)_m$thiazolyl, $(CH_2)_m$ isothiazolyl, $(CH_2)_m$phenyl, $(CH_2)_m$pyrrolyl, $(CH_2)_m$ pyridyl, or $(CH_2)_m$pyrimidyl, which cycloalkyl and said cycloalkenyl groups optionally contain one or two heteroatoms selected independently from O, N, and S, and which alkyl, cycloalkyl, cycloalkenyl, alkenyl, alkynyl, imidazolyl, pyrazyl, oxazolyl, isoxazolyl, thiazolyl, isothiazolyl, phenyl, pyrrolyl, pyridyl, or pyrimidyl groups are optionally substituted with one or two groups selected, independently, from OH, halogen, cyano, methyl, ethyl, or trifluoromethyl, where m is zero, 1, or 2; or $R_1$ and $R_2$, together with the ring carbon atoms to which they are attached, form a 5- or 6-member fused ring, which ring. may be saturated, unsaturated, or aromatic, which optionally contains one or two heteroatoms selected independently from O, N, and S, and which is optionally substituted with halogen, $CF_3$, or $C_1$-$C_3$ alkyl; R' is H, halogen, $CF_3$, or $C_1$-$C_3$ alkyl; $R_3$ and $R_4$ are, independently, H, $NH_2$, ($C_1$-$C_3$ alkyl)NH, CN, halogen, $CF_3$, $OCF_3$, $OC_1$-$C_3$ alkyl, or $C_1$-$C_3$ alkyl, all said $C_1$-$C_3$ alkyl groups and said $C_1$-$C_6$ alkyl groups optionally substituted with one or two groups selected, independently, from OH, halogen, $C_1$-$C_3$ alkyl, $OC_1$-$C_3$ alkyl, or trifluoromethyl; q=1 or 0; $R_5$ is $C_1$-$C_6$ alkyl, $(CHR_6)_w C_3$-$C_6$ cycloalkyl, $(CHR_6)$o, $CH_2 C_3$-$C_6$ cycloalkyl, $CH_2 (CHR_6)_w C_3$-$C_6$ cycloalkyl, $CR_6$=CH—$C_3$-$C_6$ cycloalkyl, CH=$CR_6$—$C_3$-$C_6$ cycloalkyl, $(CHR_6)_w C_5$-$C_6$ cycloalkenyl, $CH_2 (CHR_6)_w C_5$-$C_6$ cycloalkenyl, $C_2$-$C_6$ alkenyl, $C_2$-$C_6$ alkynyl, $Ar_1$, $(CHRAr_1$, $CH_2(CHR_6)_w Ar_1$, or $(CHR_6)_w CH_2 Ar_1$, where w=0-3, $Ar_1$ is phenyl, pyridyl, furyl, thienyl, pyrrolyl, oxazolyl, thiazolyl, or imidazolyl where the $C_1$-$C_6$ alkyl group is optionally substituted with hydroxy, methoxy, methylthio, or halogen, and where the cycloalkyl and cycloalkenyl groups are optionally substituted with one or two groups selected, independently, from OH, halogen, cyano, methyl, ethyl, or trifluoromethyl; $R_6$ is hydrogen, methyl, halogen, or methoxy; and pharmaceutically acceptable salts thereof. Such compounds are potassium channel modulators.

In another embodiment, this invention provides or contemplates a composition comprising a pharmaceutically acceptable carrier, excipient or diluent and at least one of the following: i) a pharmaceutically effective amount of a compound of formula I; ii) a pharmaceutically acceptable salt thereof; iii) a pharmaceutically acceptable ester thereof; iv) and a pharmaceutically acceptable solvate thereof.

In another embodiment, this invention provides or contemplates a method of treating or preventing a disease or disorder which is affected by enhancement of neural M currents comprising administering to a patient in need thereof one or more of the following: i) a pharmaceutically effective amount of a compound of formula I; ii) a pharmaceutically acceptable salt thereof; iii) a pharmaceutically acceptable ester thereof; iv) and a pharmaceutically acceptable solvate thereof.

In yet another embodiment, this invention provides a method of preventing or treating a disease or disorder which is affected by activation of voltage-gated potassium channels, comprising administering to a patient in need thereof one or more of the following: a pharmaceutically effective amount of a compound of formula I; ii) a pharmaceutically acceptable salt thereof; iii) a pharmaceutically acceptable ester thereof; and iv) a pharmaceutically acceptable solvate thereof.

In yet another embodiment, this invention provides or contemplates a method of treating or preventing a seizure disorder in a human comprising administering to a patient afflicted or potentially afflicted with such disorder one or more of the following: a pharmaceutically effective amount of a compound of formula I; ii) a pharmaceutically acceptable salt thereof; iii) a pharmaceutically acceptable ester thereof; iv) and a pharmaceutically acceptable solvate thereof.

In another embodiment, this invention provides or contemplates a pharmaceutical formulation for oral administration comprising a therapeutically effective amount of a compound of formula I and either an appropriate tabletting agent or an appropriate syrup for pediatric use.

In another embodiment, this invention provides or contemplates a tablet for oral administration comprising a therapeutically effective amount of a compound of formula I and an appropriate tabletting agent.

In another appropriate embodiment, this invention provides or contemplates a syrup for pediatric use comprising a solution or dispersion or suspension of a compound of formula I and an appropriate syrup.

In another embodiment, this invention contemplates a pharmaceutical formulation for administration to animals, including companion animals (dogs and cats), and livestock comprising a therapeutically effective amount of a compound of formula I and a veterinary acceptable carrier.

In another embodiment, this invention contemplates a method of preventing or treating a disease or disorder which is affected by activation of voltage-gated potassium channels comprising administering to an animal in need thereof one or more of the following: i) a pharmaceutically effective amount of a compound of formula I; ii) a pharmaceutically acceptable salt thereof; iii) a pharmaceutically acceptable ester thereof; iv) and a pharmaceutically acceptable solvate thereof.

In another embodiment, this invention contemplates a method of treating a seizure disorder in an animal comprising administering to an animal afflicted or potentially afflicted with such a disorder one or more of the following: i) a pharmaceutically effective amount of a compound of formula I; ii) a pharmaceutically acceptable salt thereof; iii) a pharmaceutically acceptable ester thereof; iv) and a pharmaceutically acceptable solvate thereof.

This invention includes all tautomers, salts, and stereoisomeric forms of compounds of formula I. This invention also includes all compounds of this invention where one or more atoms are replaced by a radioactive isotope thereof.

In a more specific subgeneric embodiment, the invention provides a compound of formula IA

IA

In another more specific subgeneric embodiment, this invention provides a compound of formula IB.

IB

In a still more specific subgeneric embodiment, this invention provides a compound of formula IA, where W and Z are both N.

In another still more specific subgeneric embodiment, this invention provides a compound of formula IA, where W is N and Z is CH.

In another still more specific subgeneric embodiment, this invention provides a compound of formula IA, where W is CH and Z is N.

In another more specific subgeneric embodiment, this invention provides a compound of formula IA, where R' is H, halogen, $CF_3$, or methyl.

In another more specific subgeneric embodiment, this invention provides a compound of formula IA, where W and Z are both N and R' is H, F, or methyl.

In another more specific subgeneric embodiment, the invention provides a compound of formula IB, where W and Z are both N.

In another more specific subgeneric embodiment, this invention provides a compound of formula IB, where W is N and Z is CH.

In another more specific subgeneric embodiment, this invention provides a compound of formula IB, where W is CH and Z is N.

In another more specific subgeneric embodiment, this invention provides a compound of formula IB, where R' is H, halogen, $CF_3$, or methyl.

In another more specific subgeneric embodiment, this invention provides a compound of formula IB, where W and Z are both N and R' is H, F, or methyl.

In a more specific subgeneric embodiment, this invention provides or contemplates a compound of formula IA, where $R_5$ is $C_1$-$C_6$ alkyl, $(CHR_6)$, $NC_3$-$C_6$ cycloalkyl, $(CHR_6)_w$ $CH_2C_3$-$C_6$ cycloalkyl, or $CH_2$ $(CHR_6)_w C_3$-$C_6$ cycloalkyl.

In a more specific subgeneric embodiment, this invention provides or contemplates a compound of formula IB, where $R_5$ is $C_1$-$C_6$ alkyl, $(CHR_6)_w$, $C_3$-$C_6$ cycloalkyl, $(CHR_6)_w$ $CH_2C_3$-$C_6$ cycloalkyl, or $CH_2$ $(CHR_6)_w C_3$-$C_6$ cycloalkyl.

In a still more specific subgeneric embodiment, this invention provides or contemplates a compound of formula IA, where $R_5$ is $C_1$-$C_6$ alkyl, $(CHR_6)C_3$-$C_6$ cycloalkyl, $(CHR_6)_w$ $CH_2C_3$-$C_6$ cycloalkyl, or $CH_2$ $(CHR_6)_w C_3$-$C_6$ cycloalkyl; and $R_1$ is H, $CF_3$, or halogen.

In a still more specific subgeneric embodiment, this invention provides or contemplates a compound of formula IA, where R5 is $C_1$-$C_6$ alkyl, substituted with methoxy, methylthio, or halogen; R' is methyl or H; and $R_1$ is H, $CF_3$, or halogen.

In another subgeneric embodiment, this invention provides or contemplates a compound of formula I, where $R_5$ is $CR_6$=CH—$C_3$-$C_6$ cycloalkyl, CH=$CR_6$—$C_3$-$C_6$ cycloalkyl, $(CHR_6)_w C_5$-$C_6$ cycloalkenyl, $CH_2$ $(CHR_6)_w C_5$-$C_6$ cycloalkenyl, $C_2$-$C_6$ alkenyl, or $C_2$-$C_6$ alkynyl; R' is methyl or H; and $R_1$ is H, $CF_3$, or halogen.

In another more specific subgeneric embodiment, this invention provides or contemplates a compound of formula IA, where R' is methyl or H; $R_1$ is H, $CF_3$, or halogen; $R_3$ and $R_4$ are methyl, aminomethyl, or chloro; and $R_5$ is $Ar_1$, $(CHR_6)_w Ar_1$, $CH_2 (CHR_6)_w Ar_1$, or $(CHR_6)_w CH_2 Ar_1$.

In another more specific subgeneric embodiment, this invention provides or contemplates a compound of formula IA, where R' is methyl or H; $R_1$ is H, $CF_3$, or halogen; $R_3$ and $R_4$ are methyl; and $R_5$ is $C_1$-$C_6$ alkyl, $(CHR_6)_w C_3$-$C_6$ cycloalkyl, $(CHR_6)CH_2C_3$-$C_6$ cycloalkyl, or $CH_2 (CHR_6)$ C3-$C_6$ cycloalkyl.

In another more specific subgeneric embodiment, this invention provides or contemplates a compound of either of formulas IA or IB, where $R_2$ is H or F; R' is H or halogen; $R_3$ and $R_4$ are methyl; and $R_5$ is $C_1$-$C_6$ alkyl, $(CHR_6)_w C_3$-$C_6$ cycloalkyl, $(CHR_6)_w CH_2 C_3$-$C_6$ cycloalkyl, or $CH_2 (CHR_6)_w$ $C_3$-$C_6$ cycloalkyl.

In another more specific subgeneric embodiment, this invention provides or contemplates a compound of formula IA or formula IB, where RS is CHZCHZcyclopentyl or one of the groups below:

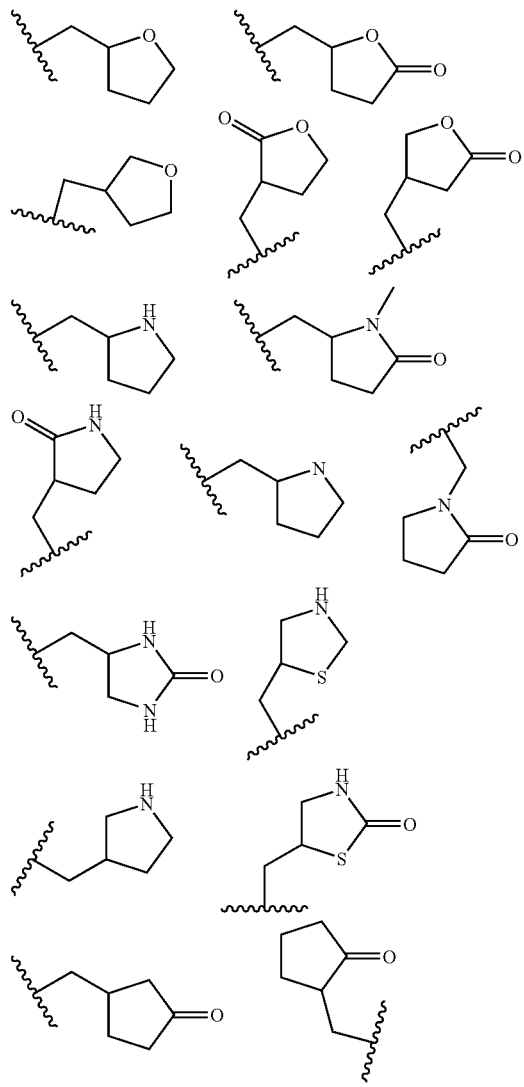

In another more specific subgeneric embodiment, this invention provides or contemplates a compound of formula IA or IB where $R_1$ is halogen or halomethyl; $R_2$ is H, or halogen; and $R_5$ is one of the groups above.

In another more specific subgeneric embodiment, this invention provides or contemplates a compound of formula IA or IB, where $R_1$ is phenyl, pyridyl, pyrrolyl, $(CH_2)_m$imidazolyl, $(CH_2)_m$pyrazyl, $(CH_2)_m$oxazolyl, $(CH_2)_m$isoxazolyl, $(CH_2)_m$thiazolyl, $(CH_2)_m$isothiazolyl, $(CH_2)_m$phenyl, $(CH_2)_m$ pyrrolyl, $(CH_2)_m$pyridyl, or $(CH_2)_n$pyrimidyl, and $R_5$ is $C_5$-$C_6$ alkyl or $CH_2$—$C_3$-$C_6$ cycloalkyl.

The examples below are provided to show—but not to limit in any way—the variety of possible embodiments of this invention

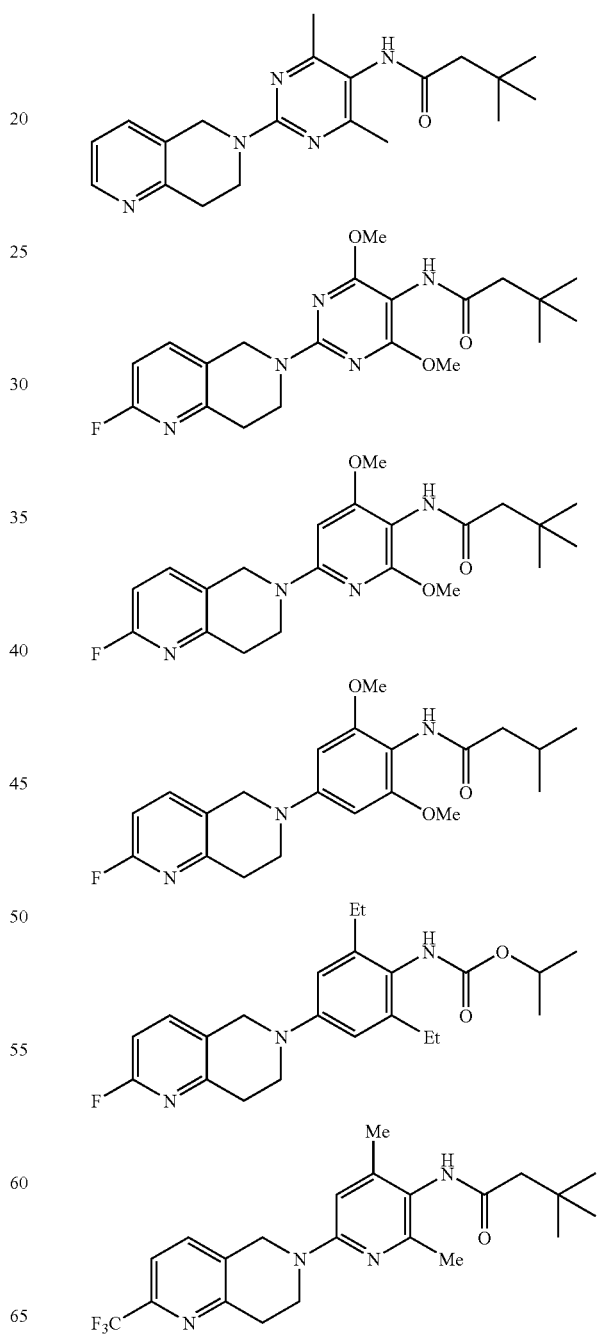

-continued
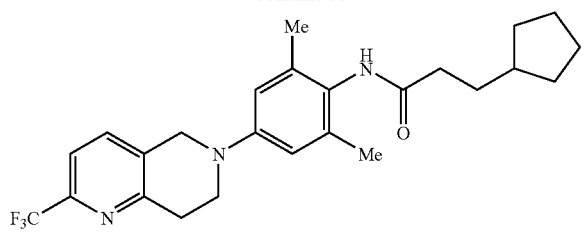
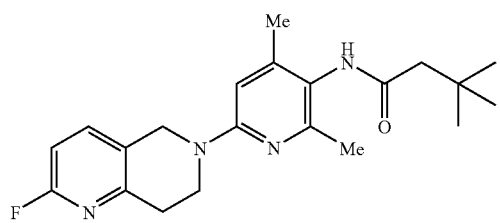
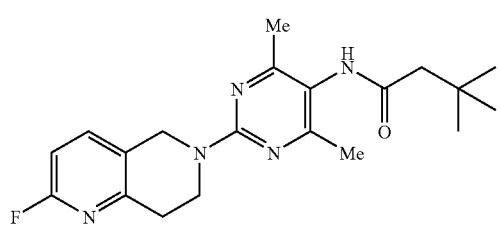
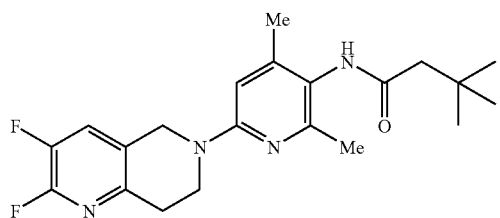
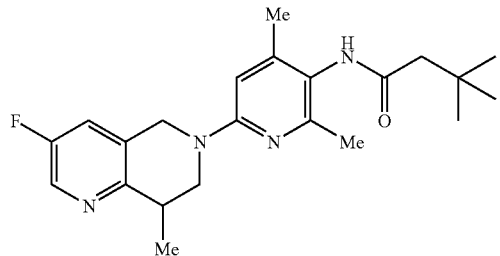
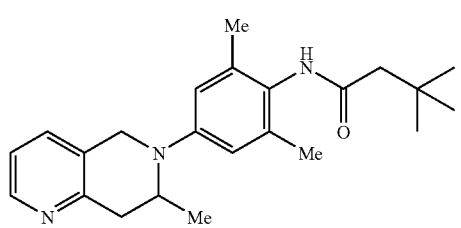
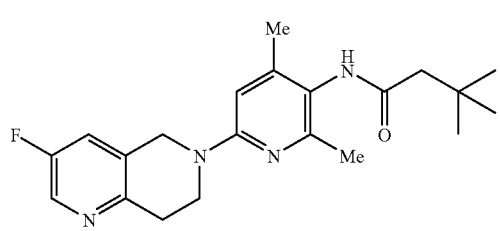
-continued
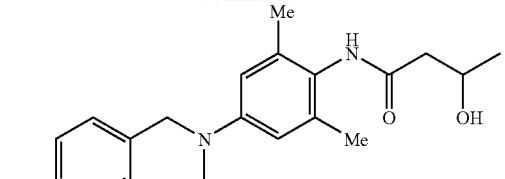
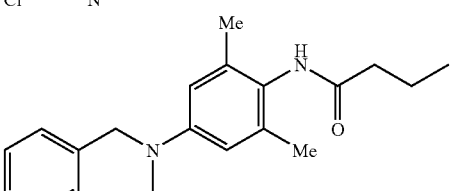
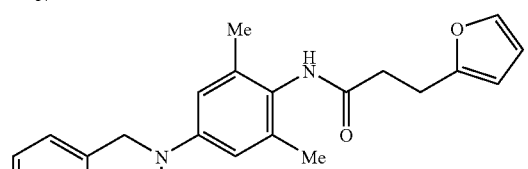
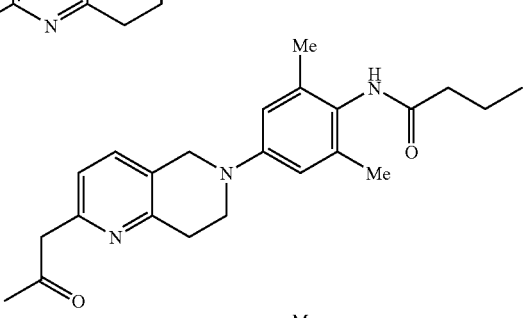
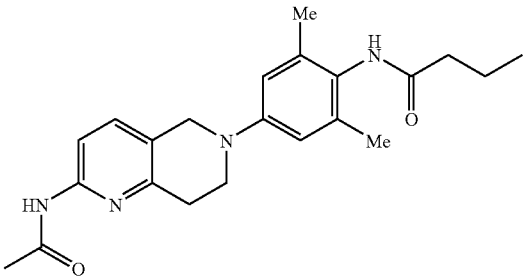
DETAILED DESCRIPTION OF THE INVENTION
In designing compounds with therapeutic properties superior to those of retigabine,
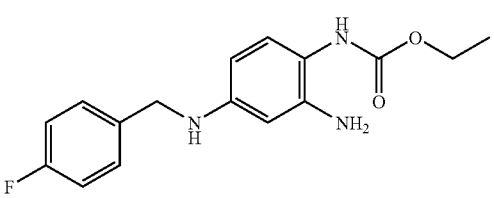
retigabine
the present inventors have discovered that para N-1,2,3,4-tetrahydro isoquinolyl anilides and carbamates of the structure of formula I

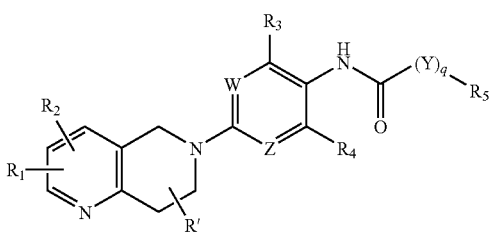

I have surprising and exceptional activity toward potassium channels, as evidenced by their potent activities, as measured in the rubidium efflux assay described below.

As used herein the term "potassium channel modulator" refers to a compound capable of causing an increase in potassium channel currents. It also refers to a compound capable of increasing the KCNQ2/3 channel open probability. For preliminary testing of compounds for potassium channel modulating ability, the inventors have employed the rubidium ion efflux test described below.

As contemplated by this invention, compounds of formula I are designed for oral or intravenous dosing of up to approximately 1200 mg per day. Thus, this invention contemplates solutions and suspensions of compounds of formula I formulated for intravenous administration. Similarly, solutions and suspensions comprising a syrup such as sorbitol or propylene glycol, among many other examples, in addition to compounds of formula I, suitable for oral pediatric administration, are also contemplated. Additionally, both chewable and non-chewable tablets comprising compounds of formula I, along with pharmaceutically acceptable tabletting agents and other pharmaceutically acceptable carriers and excipients, are also contemplated. As used herein, the term pharmaceutically acceptable carrier comprises such excipients, binders, lubricants, tabletting agents and disintegrants as are typically used in the art of formulation of pharmaceuticals. Examples of such agents include—but are not limited to—microcrystalline cellulose, lactose, starch, and dicalcium phosphate, and Providone. Additionally, disintegrants such as sodium starch glycolate, lubricants such as stearic acid and $SiO_2$, and solubility enhancers such as cyclodextrins, among many other examples for each group, are contemplated. Such materials and the methods of using them are well known in the pharmaceutical art. Additional examples are provided in Kibbe, Handbook of Pharmaceutical Excipients, London, Pharmaceutical Press, 2000.

The invention also contemplates pharmaceutical formulations, including vaccine formulations, for administration to animals, including companion animals (dogs and cats) and livestock, such as cattle, pigs, sheep and horses comprising a therapeutically effective amount of a compound of formula I and a veterinary acceptable carrier. However, any animal that is susceptible to seizure disorders is included within the scope of this invention. The typical mode of administration will be intramuscular, oral or subcutaneous injection of between about 0.05 ml and 25 ml of vaccine formulation. However, as indicated above, the compounds of formula I are designed to be dosed up to approximately 1200 mg per day. Vaccination can be accomplished by a single inoculation or via several inoculations. The contemplated vaccine compositions utilized in the methods of the present invention can include one or more veterinary-acceptable carriers. A "veterinary-acceptable carrier" includes any and all solvents, dispersion media, coatings adjuvants, stabilizing agents; diluents, excipients, preservatives, isotonic agents. Diluents can include water, saline, dextrose, ethanol, glycerol and the like. Isotonic agents can include sodium chloride, dextrose, mannitol, serbitol and lactose, for example. Adjuvants contemplated by the present invention include, saponin, cholesterol, aluminum hydroxide gel, Freund's complete and incomplete adjuvants. The present invention also contemplates vaccine formulations comprising from about 1 mg/ml to about 2000 mg of adjuvant/dose of the vaccine composition.

Synthetic Chemistry

General Schemes

Section I.

The preparation of compounds of formula V is outlined in Scheme I.

Scheme 1:

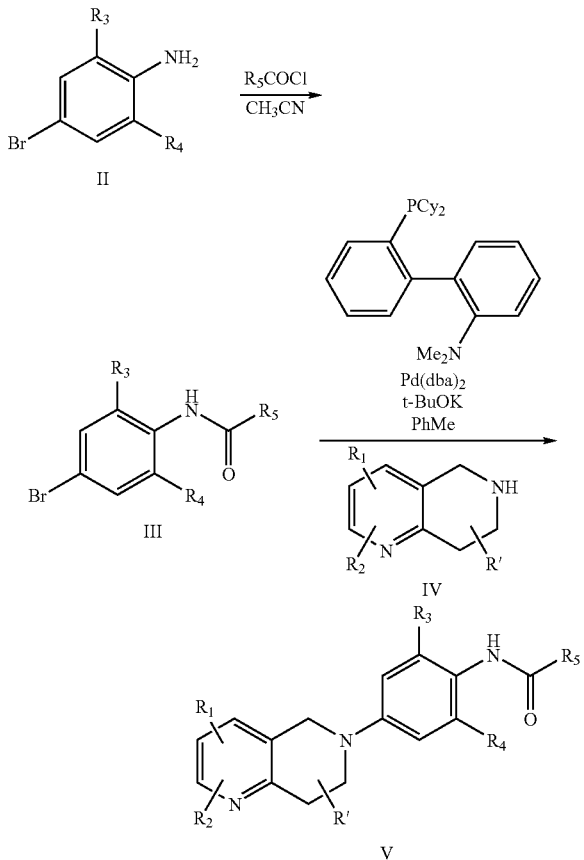

Section II.

The preparation of compounds of formula VII is outlined in Scheme 2.

Scheme 2:

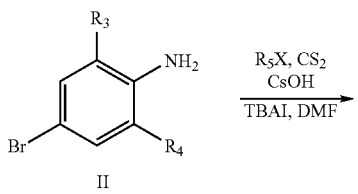

-continued
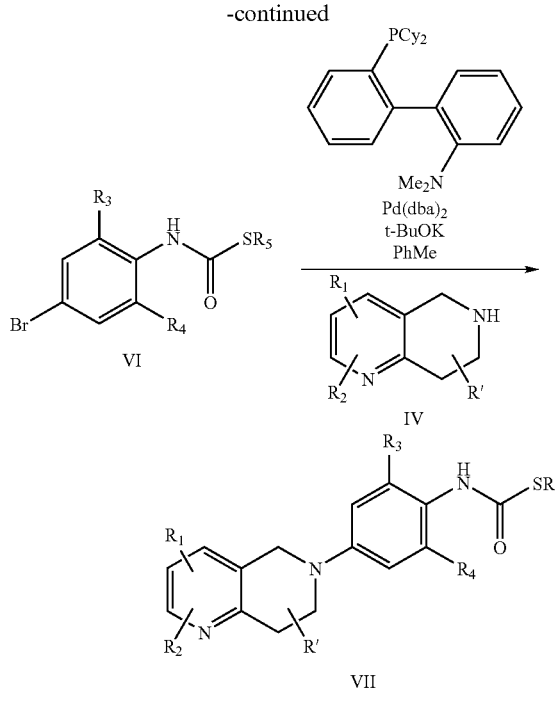
Section III.
The preparation of compound of formula IX is outlined in Scheme 3.
Scheme 3:
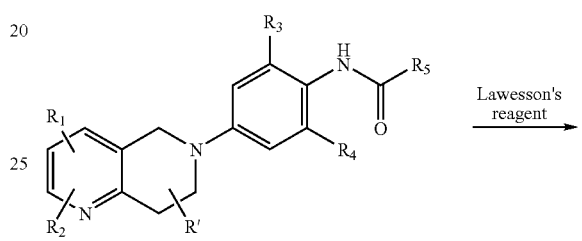
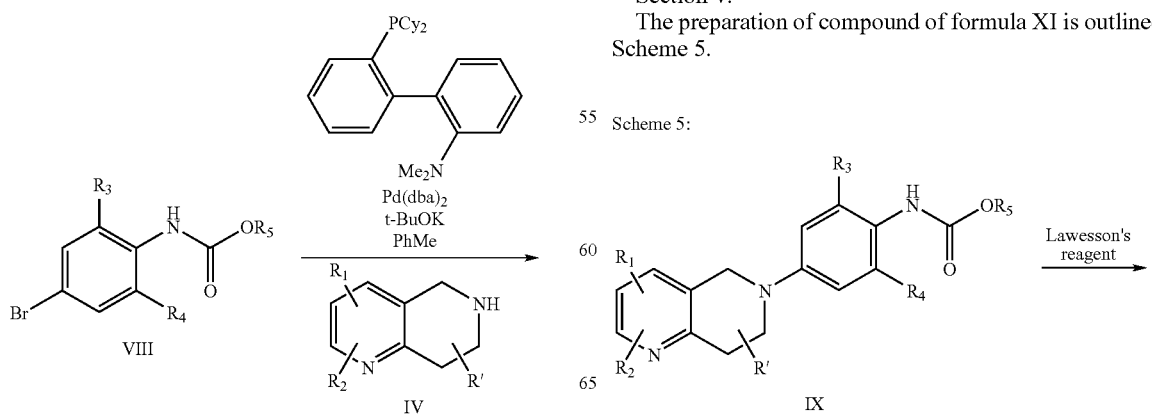
Section IV.
The preparation of compound of formula X is outlined in Scheme 4.
Scheme 4:
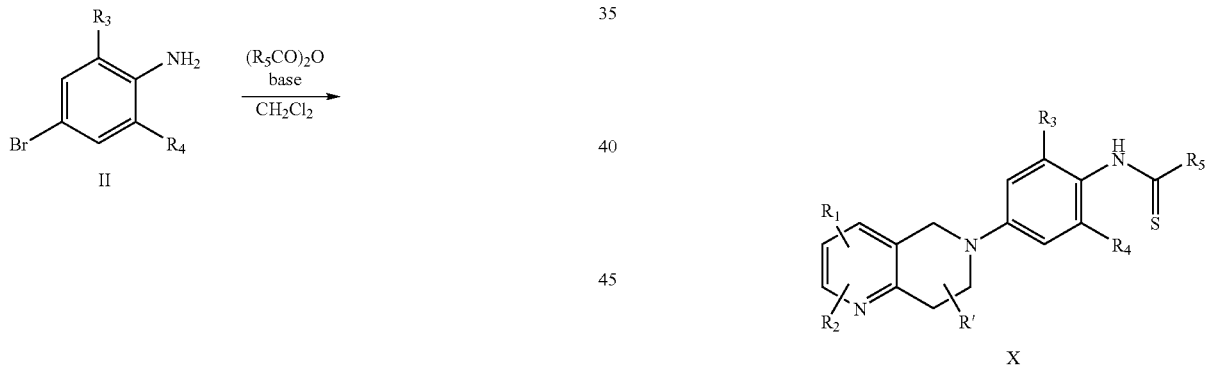
Section V.
The preparation of compound of formula XI is outlined in Scheme 5.
Scheme 5:

-continued
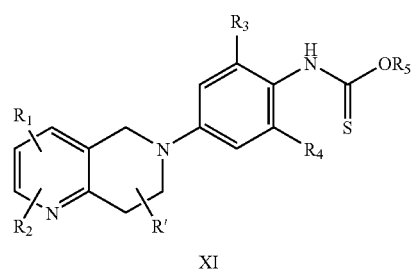
Section VI.
The preparation of compound of formula XIII is outlined in Scheme 6.
Scheme 6:
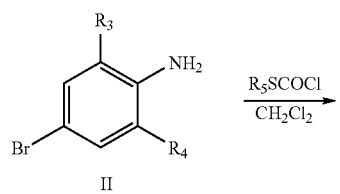
-continued
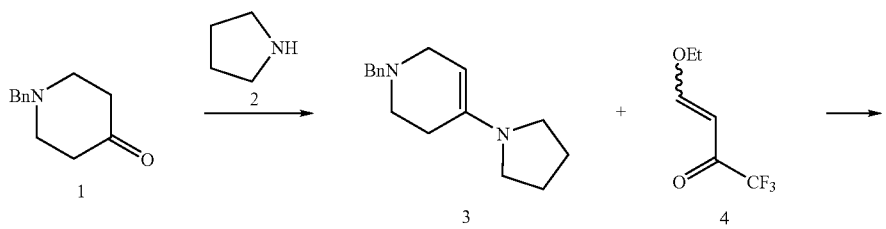
Preparation of Particular Compounds
Synthesis of N-[2,6-dimethyl-4-(2-trifluoromethyl-7,8-dihydro-5H-[1,6]naphthyridin-6-yl)-phenyl]-3,3-dimethyl-butyramide (11)
Scheme I
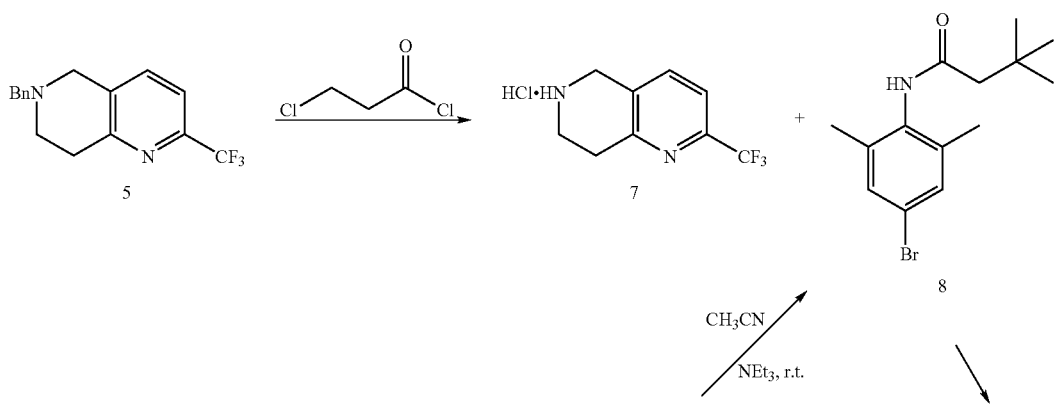

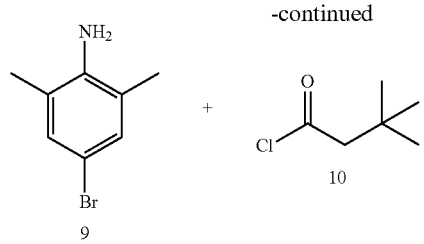 + 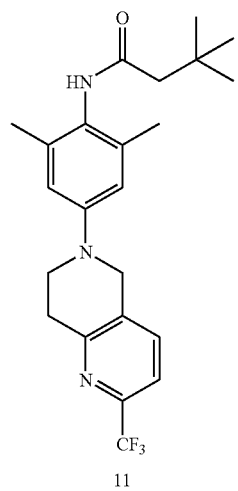

1-Benzyl-4-pyrrolidin-1-yl-1,2,3,6-tetrahydropyridine (3)

A solution containing N-benzyl piperidone 1 (5 g, 26.4 mmol) and pyrrolidine 2 (2.82 g, 39.6 mmol) in toluene (60 mL) was heated to reflux with azeotropic removal of water. The reaction mixture was then cooled and concentrated under reduced pressure. The resulting oil was dissolved in ether, dried over magnesium sulfate, and concentrated under reduced pressure. The crude enamine 3 was used in the next step.

6-Benzyl-2-trifluoromethyl-5,6,7,8-tetrahydro-[1,6]naphthyridine (5)

To a solution of the crude enamine 3 (500 mg, 2.1 mmol) in dioxane (5 mL) was added compound 4 (0.3 mL, 2.1 mmol), and the mixture was stirred at room temperature overnight. Ammonium acetate (20 mg) was then added, and the mixture was heated at reflux for 18 h. The reaction mixture was then cooled to room temperature, acidified with 10% HCl, extracted with dichloromethane, and concentrated. Purification by preparative thin layer chromatography (DCM/MeOH 5%) afforded compound 5.

2-Trifluoromethyl-5,6,7,8-tetrahydro-[1,6]naphthyridine (7)

To a solution of 5 (500 mg, 1.7 mmol) in dichoromethane (8 mL) was added compound 6, 3-chloro propionyl chloride (0.22 mL, 2.1 mmol) and the reaction mixture was stirred at 40° C. for 18 h. The reaction was then cooled to room temperature and concentrated. The resulting residue was dissolved in methanol (16 mL) and stirred at 40° C. for 3 h. The mixture was then cooled to room temperature and concentrated.

N-(4-Bromo-2,6-dimethyl-phenyl)-3,3-dimethyl-butyramide (8)

3,3-dimethylbutanoyl chloride (3.37 g, 3.5 mL, 25 mmol) and triethylamine (2.53 g, 3.5 mL, 25 mmol) were added to a solution of 4-bromo-2-chloro-6-(trifluoromethyl)aniline (5.0 g, 25 mmol) in acetonitrile (30 mL). The reaction mixture was stirred at room temperature for 4 hours. Water was added to the mixture, and the precipitate formed collected to give the title compound as a powder (7.46 g, 100% yield).

N-[2,6-Dimethyl-4-(2-trifluoromethyl-7,8-dihydro-5H-[1,6]naphthyridin-6-yl)-phenyl]-3,3-dimethyl-butyramide (11)

Bis(dibenzylidineacetone)palladium (15 mg, 0.026 mmol) and (2'-dicyclohexyl phosphanyl-biphenyl-2-yl)-dimethylamine (40 mg, 0.1 mmol) were added to dry toluene (5 mL purged with argon for 30 min), and the mixture was stirred for an additional 30 minutes at room temperature under argon. Potassium tert-butoxide (188 g, 71 mmol), compound 7 (191 mg, 0.8 mmol), aid compound 8 (200 mg, 0.67 mmol) were then added; the reaction mixture was stirred at 80° C. overnight. The reaction mixture was then cooled to room temperature, filtered through a pad of silica gel, and purified by preparative TLC (DCM/MeOH 5%) to afford compound 11.

N-(2,6-dimethyl-4-(3-(trifluoromethyl)-7,8-dihydro-1,6-naphthyridin-6(5H)-yl)phenyl)-3,3-dimethylbutanamide

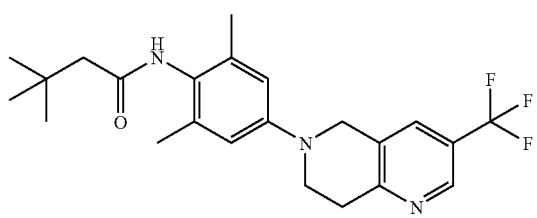 [SMILES: Cc1cc(N2CCc3ncc(C(F)(F)F)cc3C2)cc(C)c1NC(=O)CC(C)(C)C]

Bis(dibenzylidineacetone)palladium (4 mg, 0.069 mmol) and (2'-dicyclohexylphosphanyl-biphenyl-2-yl)-dimethylamine (7 mg, 0.015 mmol) were added to dry toluene (1 mL purged with argon) and stirred for 15 minutes under argon. Potassium tert-butoxide (36 mg, 0.32 mmol), N-(4-bromo-2,6-dimethylphenyl)-3,3-dimethylbutanamide (52 mg, 0.17 mmol) and 3-(trifluoromethyl)-5,6,7,8-tetrahydro-1,6-naphthyridine (WO/04069162) (40 mg, 0.15 mmol) were then added and the reaction mixture was stirred at 80° C. overnight. The reaction mixture was then cooled to room temperature, concentrated and purified by biotage (75% Ethyl acetate: Hexanes) to afford the desired compound as a solid. $^1$H NMR (DMSO-$d_6$, 400 MHz) δ 1.05 (s, 9H), 2.11 (s, 6H), 2.17 (s, 2H), 3.08 (t, J=5.6 Hz, 2H), 3.64 (t, J=5.9 Hz, 2H), 4.48 (s, 2H), 6.76 (s, 2H), 8.08 (s, 1H), 8.75 (s, 1H), 8.90 (s, 1H).

Synthesis of other substituted tetrahydro-1,6-naphthyridines

Substitution at positions 2 and 3 of tetrahydro-1,6-naphthyridines can be accomplished by the condensation of 1-benzyl-4-piperidinone with the corresponding 3-amino-enones followed by debenzylation. (Scheme II)

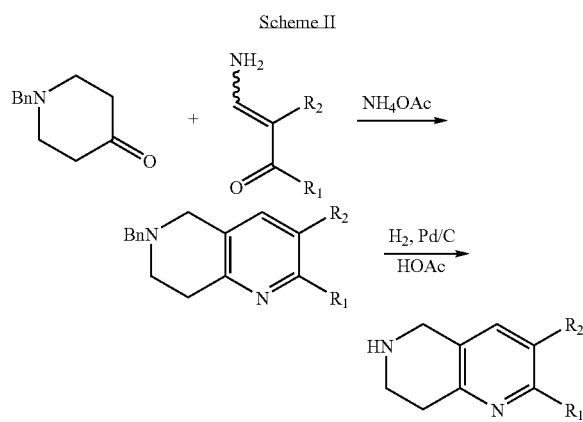

Alkylation at the 5- or 8-position of tetrahydro-1,6-naphthyridines can be accomplished by chemical modification of pyridine derivatives. (See Scheme III)

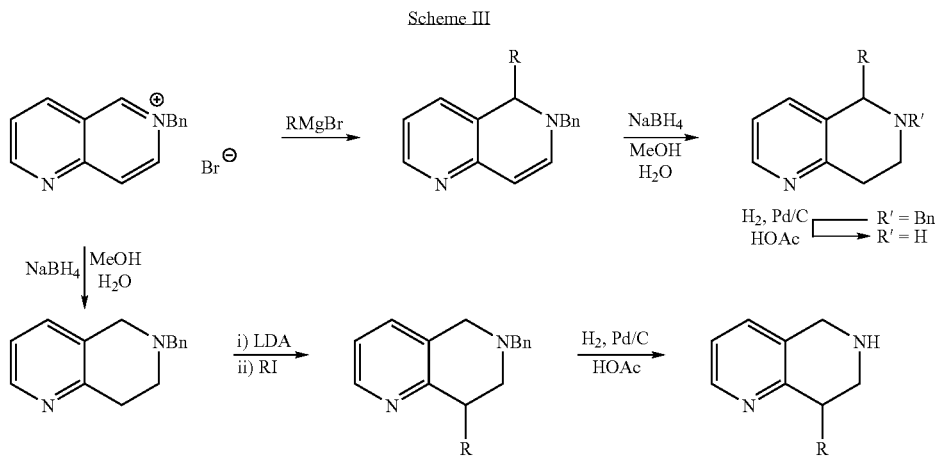

Biological Results

Compounds of this invention formula were evaluated as potassium channel modulators by measuring rhubidium ion release in the following assay.

Methods:

PC-12 cells were grown at 37° C. and 5% $CO_2$ in DMEM/F12 Medium supplemented with 10% horse serum, 5% fetal bovine serum, 2 mM glutamine, 100 U/ml penicillin, 100 U/ml streptomycin. They were plated in poly-D-lysine-coated 96-well cell culture microplates at a density of 40,000 cells/well and differentiated with 100 ng/ml NGF-7s for 2-5 days. For the assay, the medium was aspirated, and the cells were washed once with 0.2 ml in wash buffer (25 mM HEPES, pH 7.4, 150 mM NaCl, 1 mM $MgCl_2$, 0.8 mM $NaH_2PO_4$, 2 mM $CaCl_2$). The cells were then loaded with 0.2 ml $Rb^+$ loading buffer (wash buffer plus 5.4 mM $RbC_2$, 5 mM glucose) and incubated at 37° C. for 2 h. Attached cells were quickly washed three times with buffer (same as $Rb^+$ loading buffer, but containing 5.4 mM KCl instead of RbCl) to remove extracellular $Rb^+$. Immediately following the wash, 0.2 ml of depolarization buffer (wash buffer plus 15 mM KCl) with or without compounds was added to the cells to activate efflux of potassium ion channels. After incubation for 10 min at room temperature, the supernatant was carefully removed and collected. Cells were lysed by the addition of 0.2 ml of lysis buffer (depolarization buffer plus 0.1% Triton X-100) and the cell lysates were also collected. If collected samples were not immediately analyzed for $Rb^+$ contents by atomic absorption spectroscopy (see below), they were stored at 4° C. without any negative effects on subsequent $Rb^+$ analysis.

The concentration of $Rb^+$ in the supernatants ($Rb^+_{sup}$) and cell lysates ($Rb^+_{Lys}$) was quantified using an ICR8000 flame atomic absorption spectrometer (Aurora Biomed Inc., Vancouver, B.C.) under conditions defined by the manufacturer. One 0.05 ml samples were processed automatically from microtiter plates by dilution with an equal volume of $Rb^+$ sample analysis buffer and injection into an air-acetylene flame. The amount of $Rb^+$ in the sample was measured by absorption at 780 nm using a hollow cathode lamp as light source and a PMT detector. A calibration curve covering the range 0-5 mg/L Rb in sample analysis buffer was generated with each set of plates. The percent $Rb^+$ efflux (F) was defined by $$F=[Rb^+_{sup}/(Rb^+_{sup}+Rb^+_{Lys})] \times 100\%$$

The effect (E) of a compound was defined by: $E=[(F_c-F_b)/(F_s-F_b)] \times 100\%$ where the $F_c$ is the efflux in the presence of compound in depolarization buffer, $F_b$ is the efflux in basal buffer, and $F_s$ is the efflux in depolarization buffer, and F is the efflux in the presence of compound in depolarization buffer. The effect (E) and compound concentration relationship was plotted to calculate an $EC_{50}$ value, a compound's concentration for 50% of maximal Rb+ efflux. The results are shown below. Legend: A: $EC_{50}$ 1 nM–50 nM; B: $EC_{50}$=50 nM–100 nM; C: $EC_{50}$=100–500 nM

TABLE 1

ACTIVITY OF EXEMPLARY COMPOUND

| COMPOUND | ACTIVITY |
|---|---|
| 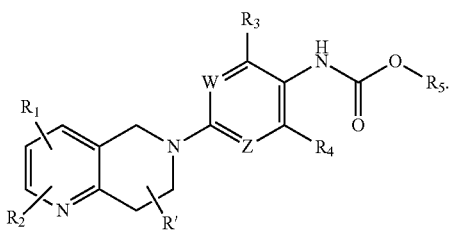 | A |
| 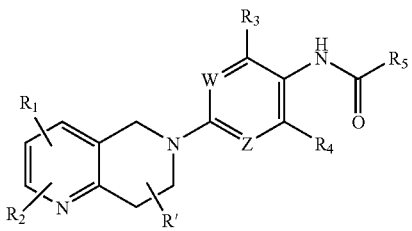 retigabine | C |

What is claimed is:

1. A compound of formula IB

IB where W and Z are, independently, CH or N;
where $R_1$ and $R_2$, are, independently, H, halogen, $CH_2F$, $CHF_2$, $CF_3$, $CF_2CF_3$, $C_1$-$C_6$ alkyl, C(=O)$C_1$-$C_6$ alkyl, $CH_2$C(=O)$C_1$-$C_6$ alkyl, NH—$C_1$-$C_6$ alkyl, NHC(=O)$C_1$-$C_6$ alkyl, C(=O)N(CH$_3$)$_2$, C(=O)N(Et)$_2$, C(=O)NH—$C_1$-$C_6$ alkyl, C(=O)O$C_1$-$C_6$ alkyl, OC(=O)$C_1$-$C_6$ alkyl, O$C_1$-$C_6$ alkyl, S$C_1$-$C_6$ alkyl, $C_3$-$C_6$ cycloalkyl, (CH$_2$)$_m$$C_3$-$C_6$ cycloalkyl, $C_3$-$C_6$ cycloalkenyl, (CH$_2$)$_m$$C_3$-$C_6$ cycloalkenyl, $C_2$-$C_6$ alkenyl, $C_2$-$C_6$ alkynyl, Ar$_1$, (CH$_2$)$_m$Ar$_1$, phenyl, pyridyl, pyrrolyl, (CH$_2$)$_m$imidazolyl, (CH$_2$)$_m$pyrazyl, furyl, thienyl, (CH$_2$)$_m$oxazolyl, (CH$_2$)$_m$isoxazolyl, (CH$_2$)$_m$thiazolyl, (CH$_2$)$_m$isothiazolyl, (CH$_2$)$_m$phenyl, (CH$_2$)$_m$pyrrolyl, (CH$_2$)$_m$pyridyl, or (CH$_2$)$_m$pyrimidyl, which cycloalkyl and said cycloalkenyl groups optionally contain one or two heteroatoms selected independently from O, N, and S, and which alkyl, cycloalkyl, cycloalkenyl, alkenyl, alkynyl, imidazolyl, pyrazyl, oxazolyl, isoxazolyl, thiazolyl, isothiazolyl, phenyl, pyrrolyl, pyridyl, or pyrimidyl groups are optionally substituted with one or two groups selected, independently, from OH, halogen, cyano, methyl, ethyl, and trifluoromethyl, where m is zero, 1, or 2;
or $R_1$ and $R_2$, together with the ring carbon atoms to which they are attached, form a 5- or 6-member fused ring, which ring may be saturated, unsaturated, or aromatic, which optionally contains one or two heteroatoms selected independently from O, N, and S, and which is optionally substituted with halogen, CF$_3$, or $C_1$-$C_3$ alkyl;

R' is H, halogen, CF$_3$, or $C_1$-$C_3$ alkyl;
$R_3$ and $R_4$ are, independently, H, NH$_2$, ($C_1$-$C_3$ alkyl)NH, CN, halogen, CF$_3$, OCF$_3$, O$C_1$-$C_3$ alkyl, or $C_1$-$C_3$ alkyl, all said $C_1$-$C_3$ alkyl groups and said $C_1$-$C_6$ alkyl groups optionally substituted with one or two groups selected, independently, from OH, halogen, $C_1$-$C_3$ alkyl, O$C_1$-$C_3$ alkyl, and trifluoromethyl;
$R_5$ is $C_1$-$C_6$ alkyl, (CHR$_6$), $C_3$-$C_6$ cycloalkyl, (CHR$_6$)$_w$CH$_2$$C_3$-$C_6$ cycloalkyl, CH$_2$(CHR$_6$)$_w$$C_3$-$C_6$ cycloalkyl, CR$_6$=CH—$C_3$-$C_6$ cycloalkyl, CH=CR$_6$—$C_3$-$C_6$ cycloalkyl, (CHR$_6$)$_w$$C_5$-$C_6$ cycloalkenyl, CH$_2$(CHR$_6$)$_w$$C_5$-$C_6$ cycloalkenyl, $C_2$-$C_6$ alkenyl, $C_2$-$C_6$ alkynyl, Ar$_1$, (CHR$_6$)$_w$Ar$_1$, CH$_2$(CHR$_6$)$_w$Ar$_1$, or (CHR$_6$)$_w$CH$_2$Ar$_1$, where w=0-3, Ar$_1$ is phenyl, pyridyl, furyl, thienyl, pyrrolyl, oxazolyl, thiazolyl, or imidazolyl, wherein said $C_1$-$C_6$ alkyl group is optionally substituted with hydroxy, methoxy, methylthio, or halogen, and where said cycloalkyl and cycloalkenyl groups are optionally substituted with one or two groups selected, independently, from OH, halogen, cyano, methoxy, methyl, ethyl and trifluoromethyl; $R_6$ is hydrogen, methyl, halogen, or methoxy; or a pharmaceutically acceptable salt thereof.

2. A compound of formula IA

IA where W and Z are CH, R' is halogen, $C_1$-$C_3$ alkyl, or H, $R_1$ and $R_2$, are, independently, H, halogen, CH$_2$F, CHF$_2$, CF$_3$, CF$_2$CF$_3$, $C_1$-$C_6$ alkyl, C(=O)$C_1$-$C_6$ alkyl, CH$_2$C(=O)$C_1$-$C_6$ alkyl, NH—$C_1$-$C_6$ alkyl, NHC(=O)$C_1$-$C_6$ alkyl, C(=O)N(CH$_3$)$_2$, C(=O)N(Et)$_2$, C(=O)NH—$C_1$-$C_6$ alkyl, C(=O)O$C_1$-$C_6$ alkyl, OC(=O)$C_1$-$C_6$ alkyl, O$C_1$-$C_6$ alkyl, S$C_1$-$C_6$ alkyl, $C_3$-$C_6$ cycloalkyl, (CH$_2$)$_m$$C_3$-$C_6$ cycloalkyl, $C_3$-$C_6$ cycloalkenyl, (CH$_2$)$_m$$C_3$-$C_6$ cycloalkenyl, $C_2$-$C_6$ alkenyl, $C_2$-$C_6$ alkynyl, Ar$_1$, (CH$_2$)$_m$Ar$_1$, phenyl, pyridyl, pyrrolyl, (CH$_2$)$_m$imidazolyl, (CH$_2$)$_m$pyrazyl, furyl, thienyl, (CH$_2$)$_m$oxazolyl, (CH$_2$)$_m$isoxazolyl, (CH$_2$)$_m$thiazolyl, (CH$_2$)$_m$isothiazolyl, (CH$_2$)$_m$phenyl, (CH$_2$)$_m$pyrrolyl, (CH$_2$)$_m$pyridyl, or (CH$_2$)$_m$pyrimidyl, which cycloalkyl and said cycloalkenyl groups optionally contain one or two heteroatoms selected independently from O, N, and S, and which alkyl, cycloalkyl, cycloalkenyl, alkenyl, alkynyl, imidazolyl, pyrazyl, oxazolyl, isoxazolyl, thiazolyl, isothiazolyl, phenyl, pyrrolyl, pyridyl, or pyrimidyl groups are optionally substituted with one or two groups selected, independently, from OH, halogen, cyano, methyl, ethyl, and trifluoromethyl, where m is zero, 1, or 2;
or $R_1$ and $R_2$, together with the ring carbon atoms to which they are attached, form a 5- or 6-member fused ring, which ring may be saturated, unsaturated, or aromatic, which optionally contains one or two heteroatoms selected independently from O, N, and S, and which is optionally substituted with halogen, CF$_3$, or $C_1$-$C_3$ alkyl;
$R_3$ and $R_4$ are, independently, H, NH$_2$, ($C_1$-$C_3$ alkyl)NH, CN, halogen, CF$_3$, OCF$_3$, O$C_1$-$C_3$ alkyl, or $C_1$-$C_3$ alkyl, all said $C_1$-$C_3$ alkyl groups and said $C_1$-$C_6$ alkyl groups optionally substituted with one or two groups selected, independently, from OH, halogen, $C_1$-$C_3$ alkyl, $OC_1$-$C_3$ alkyl, and trifluoromethyl;

$R_5$ is $C_1$-$C_6$ alkyl, $(CHR_6)_w C_3$-$C_6$ cycloalkyl, $(CHR_6)_w CH_2 C_3$-$C_6$ cycloalkyl, $CH_2(CHR_6)_w C_3$-$C_6$ cycloalkyl, $CR_6$=CH—$C_3$-$C_6$ cycloalkyl, CH=$CR_6$—$C_3$-$C_6$ cycloalkyl, $(CHR_6)_w C_5$-$C_6$ cycloalkenyl, $CH_2(CHR_6)_w C_5$-$C_6$ cycloalkenyl, $C_2$-$C_6$ alkenyl, $C_2$-$C_6$ alkynyl, $Ar_1$, $(CHR_6)_w Ar_1$, $CH_2(CHR_6)_w Ar_1$, or $(CHR_6)_w CH_2 Ar_1$, where w=0-3, $Ar_1$ is phenyl, pyridyl, furyl, thienyl, pyrrolyl, oxazolyl, thiazolyl, or imidazolyl, wherein said $C_1$-$C_6$ alkyl group is optionally substituted with hydroxy, methoxy, methylthio, or halogen, and where said cycloalkyl and cycloalkenyl groups are optionally substituted with one or two groups selected, independently, from OH, halogen, cyano, methoxy, methyl, ethyl, and trifluoromethyl; $R_6$ is hydrogen, methyl, halogen, or methoxy; or a pharmaceutically acceptable salt thereof.

3. The compound of claim 1, where W and Z are CH and R' is halogen, $C_1$-$C_3$ alkyl, or H.

4. A compound of formula IA

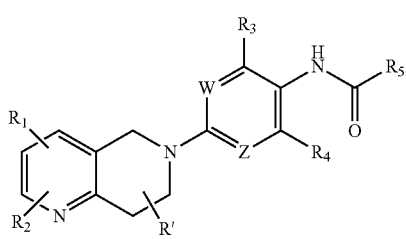

IA where W and Z are both N, R' is halogen, $C_1$-$C_3$ alkyl, or H, $R_1$ and $R_2$, are, independently, H, halogen, $CH_2F$, $CHF_2$, $CF_3$, $CF_2CF_3$, $C_1$-$C_6$ alkyl, C(=O)$C_1$-$C_6$ alkyl, $CH_2C$(=O)$C_1$-$C_6$ alkyl, NH—$C_1$-$C_6$ alkyl, NHC(=O)$C_1$-$C_6$ alkyl, C(=O)N($CH_3$)$_2$, C(=O)N(Et)$_2$, C(=O)NH—$C_1$-$C_6$ alkyl, C(=O)O$C_1$-$C_6$ alkyl, OC(=O)$C_1$-$C_6$ alkyl, O$C_1$-$C_6$ alkyl, S$C_1$-$C_6$ alkyl, $C_3$-$C_6$ cycloalkyl, $(CH_2)_m C_3$-$C_6$ cycloalkyl, $C_3$-$C_6$ cycloalkenyl, $(CH_2)_m C_3$-$C_6$ cycloalkenyl, $C_2$-$C_6$ alkenyl, $C_2$-$C_6$ alkynyl, $Ar_1$, $(CH_2)_m Ar_1$, phenyl, pyridyl, pyrrolyl, $(CH_2)_m$imidazolyl, $(CH_2)_m$pyrazyl, furyl, thienyl, $(CH_2)_m$oxazolyl, $(CH_2)_m$isoxazolyl, $(CH_2)_m$thiazolyl, $(CH_2)_m$isothiazolyl, $(CH_2)_m$phenyl, $(CH_2)_m$pyrrolyl, $(CH_2)_m$pyridyl, or $(CH_2)_m$pyrimidyl, which cycloalkyl and said cycloalkenyl groups optionally contain one or two heteroatoms selected independently from O, N, and S, and which alkyl, cycloalkyl, cycloalkenyl, alkenyl, alkynyl, imidazolyl, pyrazyl, oxazolyl, isoxazolyl, thiazolyl, isothiazolyl, phenyl, pyrrolyl, pyridyl, or pyrimidyl groups are optionally substituted with one or two groups selected, independently, from OH, halogen, cyano, methyl, ethyl, and trifluoromethyl, where m is zero, 1, or 2;

or $R_1$ and $R_2$, together with the ring carbon atoms to which they are attached, form a 5- or 6-member fused ring, which ring may be saturated, unsaturated, or aromatic, which optionally contains one or two heteroatoms selected independently from O, N, and S, and which is optionally substituted with halogen, $CF_3$, or $C_1$-$C_3$ alkyl;

$R_3$ and $R_4$ are, independently, H, $NH_2$, ($C_1$-$C_3$ alkyl)NH, CN, halogen, $CF_3$, $OCF_3$, $OC_1$-$C_3$ alkyl, or $C_1$-$C_3$ alkyl, all said $C_1$-$C_3$ alkyl groups and said $C_1$-$C_6$ alkyl groups optionally substituted with one or two groups selected, independently, from OH, halogen, $C_1$-$C_3$ alkyl, $OC_1$-$C_3$ alkyl, and trifluoromethyl;

$R_5$ is $C_1$-$C_6$ alkyl, $(CHR_6)_w C_3$-$C_6$ cycloalkyl, $(CHR_6)_w CH_2 C_3$-$C_6$ cycloalkyl, $CH_2(CHR_6)_w C_3$-$C_6$ cycloalkyl, $CR_6$=CH—$C_3$-$C_6$ cycloalkyl, CH=$CR_6$—$C_3$-$C_6$ cycloalkyl, $(CHR_6)_w C_5$-$C_6$ cycloalkenyl, $CH_2(CHR_6)_w C_5$-$C_6$ cycloalkenyl, $C_2$-$C_6$ alkenyl, $C_2$-$C_6$ alkynyl, $Ar_1$, $(CHR_6)_w Ar_1$, $CH_2(CHR_6)_w Ar_1$, or $(CHR_6)_w CH_2 Ar_1$, where w=0-3, $Ar_1$ is phenyl, pyridyl, furyl, thienyl, pyrrolyl, oxazolyl, thiazolyl, or imidazolyl, wherein said $C_1$-$C_6$ alkyl group is optionally substituted with hydroxy, methoxy, methylthio, or halogen, and where said cycloalkyl and cycloalkenyl groups are optionally substituted with one or two groups selected, independently, from OH, halogen, cyano, methoxy, methyl, ethyl, and trifluoromethyl; $R_6$ is hydrogen, methyl, halogen, or methoxy; or a pharmaceutically acceptable salt thereof.

5. The compound of claim 1, where W and Z are both N, and R' is halogen, $C_1$-$C_3$ alkyl, or H.

6. The compound of claim 1, where W is N, Z is CH, and R' is halogen, $C_1$-$C_3$ alkyl, or H.

7. The compound of claim 2, where $R_3$ and $R_4$ are, independently, methyl, amino, aminomethyl, methoxy, trifluoromethyl, or chloro.

8. The compound of claim 3, where $R_3$ and $R_4$ are, independently, methyl, amino, aminomethyl, methoxy, trifluoromethyl, or chloro.

9. The compound of claim 7, where $R_3$ and $R_4$ are, independently chloro, trifluoromethyl, methoxy, or methyl, $R_5$ is $C_5$-$C_6$ alkyl, $(CHR_6)_w CH_2 C_3$-$C_6$ cycloalkyl, or $CH_2(CHR_6)_w C_3$-$C_6$ cycloalkyl, said $C_5$-$C_6$ alkyl group optionally substituted with methoxy or halogen, and said cycloalkyl groups optionally substituted with one or two groups selected, independently, from OH, halogen, cyano, methoxy, methyl, ethyl, and trifluoromethyl.

10. The compound of claim 8, where $R_3$ and $R_4$ are, independently chloro, trifluoromethyl, methoxy, or methyl, and $R_5$ is $C_5$-$C_6$ alkyl, $(CHR_6)_w CH_2 C_3$-$C_6$ cycloalkyl, or $CH_2(CHR_6)_w C_3$-$C_6$ cycloalkyl, said $C_5$-$C_6$ alkyl group optionally substituted with methoxy or halogen, and said cycloalkyl groups optionally substituted with one or two groups selected, independently, from OH, halogen, cyano, methoxy, methyl, ethyl, and trifluoromethyl.

11. The compound of claim 9, where $R_3$ and $R_4$ are, independently chloro, trifluoromethyl, or methyl, and $R_5$ is $C_5$-$C_6$ alkyl, $(CHR_6)_w CH_2 C_3$-$C_6$ cycloalkyl, or $CH_2(CHR_6)_w C_3$-$C_6$ cycloalkyl, said $C_5$-$C_6$ alkyl group optionally substituted with methoxy or halogen, and said cycloalkyl groups optionally substituted with one or two groups selected, independently, from OH, halogen, cyano, methoxy, methyl, ethyl, and trifluoromethyl.

12. The compound of claim 10, where $R_1$ is H, halogen, $CH_2F$, $CHF_2$, $CF_3$, $CF_2CF_3$, $C_1$-$C_6$ alkyl, or C(=O)$C_1$-$C_6$ alkyl.

13. The compound of claim 11, where $R_1$ is H, halogen, $CH_2F$, $CHF_2$, $CF_3$, $CF_2CF_3$, $C_1$-$C_6$ alkyl, or C(=O)$C_1$-$C_6$alkyl.

14. The compound of claim 12, where $R_5$ is $C_5$-$C_6$ alkyl or $CH_2(CHR_6)_w C_3$-$C_6$ cycloalkyl, where w=1 and $R_6$ is H, methyl, or methoxy.

15. The compound of claim 13, where $R_5$ is $C_5$-$C_6$ alkyl or $CH_2(CHR_6)_w C_3$-$C_6$ cycloalkyl, where w=1 and $R_6$ is H, methyl, or methoxy.

16. The compound of claim 14, where $R_3$ and $R_4$ are both methyl, and $R_5$ is neopentyl or 2-cyclohexyl ethyl.

17. The compound of claim 15, where $R_3$ and $R_4$ are both methyl, and $R_5$ is neopentyl or 2-cyclohexyl ethyl.

18. The compound of claim 16, where $R_1$ is F or $CF_3$, and $R_2$ is H or F.

19. The compound of claim 17, where $R_1$ is F or $CF_3$, and $R_2$ is H or F.

20. The compound of claim 2 selected from the group consisting of:

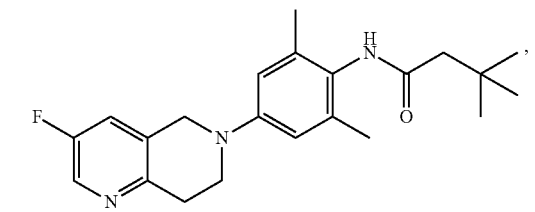

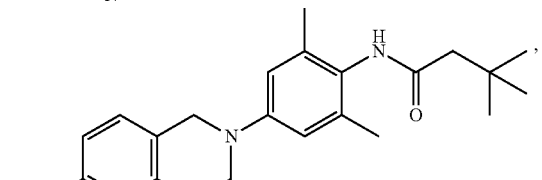

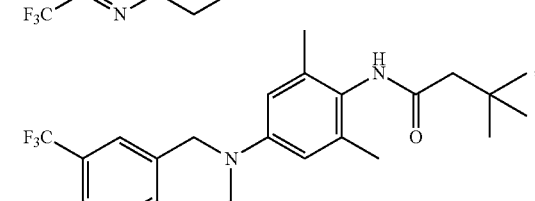

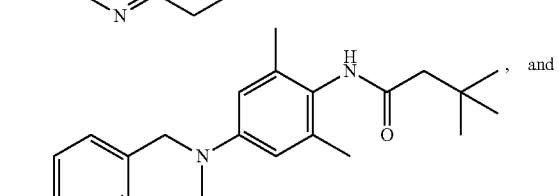

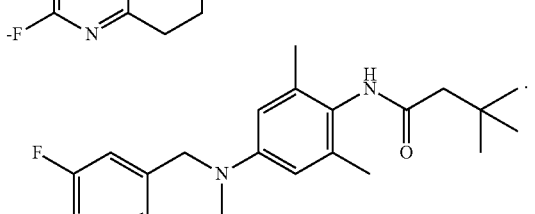

21. A composition comprising a pharmaceutically acceptable carrier and at least one of the following: i) a pharmaceutically effective amount of the compound of claim 1; and ii) a pharmaceutically acceptable salt of the compound of claim 1.

22. The composition of claim 21, in which the pharmaceutically acceptable carrier is microcrystalline cellulose.

23. A tablet for oral dosing comprising a pharmaceutically acceptable carrier and from approximately 100 to approximately 700 mg of the compound of claim 1 or a salt thereof.

24. The tablet of claim 23, further comprising a lubricant.

25. The tablet of claim 23, further comprising a disintegrant.

26. The tablet of claim 23, wherein the tablet is chewable.

27. A pharmaceutical syrup for pediatric use, comprising from approximately 100 to approximately 700 mg per dose of the compound of claim 1 or a salt thereof.

28. The compound of claim 4, wherein the compound is:

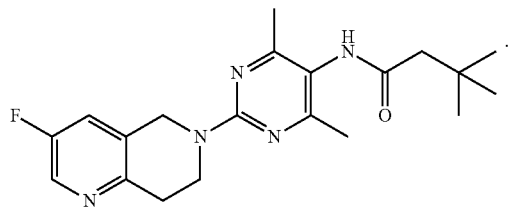

29. A compound selected from the group consisting of:

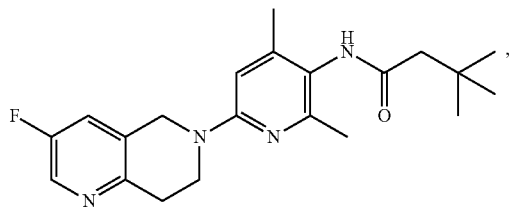

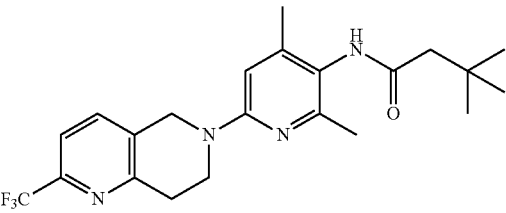 [SMILES: Cc1cc(N2CCc3nc(C(F)(F)F)ccc3C2)cc(C)c1NC(=O)CC(C)(C)C]

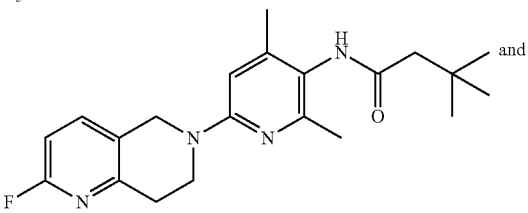

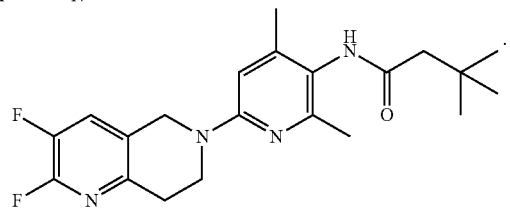

30. A composition comprising a pharmaceutically acceptable carrier and at least one of the following: i) a pharmaceutically effective amount of the compound of claim 2; and ii) a pharmaceutically acceptable salt of the compound of claim 2.

31. The composition of claim 30, in which the pharmaceutically acceptable carrier is microcrystalline cellulose.

32. A composition comprising a pharmaceutically acceptable carrier and at least one of the following: i) a pharmaceutically effective amount of the compound of claim 4; and ii) a pharmaceutically acceptable salt of the compound of claim 4.

33. The composition of claim 32, in which the pharmaceutically acceptable carrier is microcrystalline cellulose.

34. A tablet for oral dosing comprising a pharmaceutically acceptable carrier and from approximately 100 to approximately 700 mg of the compound of claim 2 or a salt thereof.

35. The tablet of claim 34, further comprising a lubricant.

36. The tablet of claim 34, further comprising a disintegrant.

37. The tablet of claim 34, wherein the tablet is chewable.

38. A pharmaceutical syrup for pediatric use, comprising from approximately 100 to approximately 700 mg per dose of the compound of claim 2 or a salt thereof.

39. A tablet for oral dosing comprising a pharmaceutically acceptable carrier and from approximately 100 to approximately 700 mg of the compound of claim 4 or a salt thereof.

40. The tablet of claim 39, further comprising a lubricant.

41. The tablet of claim 39, further comprising a disintegrant.

42. The tablet of claim 39, wherein the tablet is chewable.

43. A pharmaceutical syrup for pediatric use, comprising from approximately 100 to approximately 700 mg per dose of the compound of claim 4 or a salt thereof.

* * * * *